US007923038B2

United States Patent
Frank

(10) Patent No.: US 7,923,038 B2
(45) Date of Patent: Apr. 12, 2011

(54) METHOD AND COMPOSITION FOR THE TREATMENT OF MUSCULAR-SKELETAL AND RELATED AFFLICTIONS

(76) Inventor: Steven R. Frank, Golden, CO (US)

( * ) Notice: Subject to any disclaimer, the term of this patent is extended or adjusted under 35 U.S.C. 154(b) by 796 days.

(21) Appl. No.: 11/290,811

(22) Filed: Dec. 1, 2005

(65) Prior Publication Data

US 2006/0115544 A1    Jun. 1, 2006

Related U.S. Application Data

(60) Provisional application No. 60/631,978, filed on Dec. 1, 2004.

(51) Int. Cl.
   *A61K 36/00*    (2006.01)
   *A61K 36/53*    (2006.01)
   *A61K 36/73*    (2006.01)
   *A61K 9/00*     (2006.01)

(52) U.S. Cl. ........ 424/725; 424/745; 424/765; 424/769; 424/400

(58) Field of Classification Search ................... None
   See application file for complete search history.

(56) References Cited

U.S. PATENT DOCUMENTS 4,600,711 A * 7/1986 Swerczek .................. 514/23

OTHER PUBLICATIONS

DW-ACC 2003-169349, Jan. 2003, Derwent EP, Fabre et al.*
DW-ACC 2003-361924, Jan. 2003, Derwent, McDaniel.*
DW-ACC 1989-255684, Jul. 1989, Derwent, Yamamoto.*

* cited by examiner

Primary Examiner — Christopher R Tate
Assistant Examiner — Randall Winston
(74) Attorney, Agent, or Firm — Welsh Flaxman & Gitler LLC

(57) ABSTRACT

A method for treating musculoskeletal problems by applying a topical composition to a skin surface adjacent the musculoskeletal problem, the topical composition consisting essentially of herbal extracts in a water based synthetic gel and periodically repeating the step of applying as necessary for treatment of the musculoskeletal problem. The water based synthetic gel consists of water, Vitamin C, a carbomer, an antifungal, an anti-oxidant, a buffer and a chelate and zero alcohol. The herbal extracts are blends of the following herbs: St. John's Wort, White Willow, Yarrow, Poke, Lavender, Arnica, Comfrey, Devil's Claw, Witch Hazel, Celery Seed, Peppermint and Rosemary.

2 Claims, No Drawings

METHOD AND COMPOSITION FOR THE TREATMENT OF MUSCULAR-SKELETAL AND RELATED AFFLICTIONS

CROSS REFERENCE TO RELATED APPLICATIONS

This application claims priority of U.S. Provisional Application Ser. No. 60/631,978, entitled "METHOD AND COMPOSITION FOR THE TREATMENT OF MUSCULAR-SKELETAL AND RELATED AFFLICTIONS", filed Dec. 1, 2004.

BACKGROUND OF THE INVENTION

1. Field of the Invention

The invention relates to a method and composition for treating muscular skeletal problems. More particularly, the invention relates to the treatment of tendons, ligaments, joints and muscles, as well as the associated nerve irritation, with water-based gels formed from extracts of selected herbs.

2. Description of the Prior Art

As humans age, the soft tissues of the body begin to show significant wear and tear. This can be observed as pain relating to repetitive movements, or damage associated with activities that once were well tolerated. Contributing to these problems are muscular-skeletal misalignments, declining liver function and improper use of self and dietary insufficiencies. The results are often degradation of tendons and ligaments to the point where what once was normal use can now cause damage. Fixations can cause aggravated nerves and stiff muscles. Even joint surface problems can appear and be considered as arthritis pain.

Historically, these problems have been treated in a number of ways. Tendons and ligaments are often treated with anti-inflammatory drugs. Steroids are administered either orally or injected directly into the region of the affliction. For arthritis, systemic anti-inflammatory drugs are administered. In most cases these arthritis drugs are combined with analgesics to simply mask the pain of the condition. For muscular pain and stiffness, over-the-counter analgesics are commonly used and menthol salves are applied topically to treat the pain. These treatments are misdirected, and in some cases, even counter productive.

In the case of a soft tissue injury, such as a damaged tendon or ligament, the pain and inflammation response is necessary to initiate the healing response. Quelling this activity shortens the period of time that the body is encouraged to send repairing macrophages to the site and hence reduces the amount of repair that is completed. Inflammation is a critical part of the healing response. It is the signal that causes the generation of new restorative tissue. The use of steroids in acute cases of tendon and ligament damage can actually abort the healing process and leave the tissue poorly repaired.

In the case of arthritis due to joint erosion and surface damage, the re-building of the joint surface is critical to the restoration of pain-free movement. This is not facilitated by the topical application of analgesics and menthols. Those agents simply block nerve signals from the site to the brain producing the pain. While analgesics can be helpful in the short-term, long-term relief can only come from repairing the joint surface. The restoration of the joint will allow the inflammation and pain to cease.

During normal exercise, muscle fibers are broken and resultant repair causes increased muscle mass. This re-building of the muscle tissue is indeed the desired effect of physical conditioning and should be supported by maintaining suppleness in the tissue while encouraging good blood and lymph flow to allow the macrophages to arrive on the scene and produce restorative cells. Menthol rubs and systemic analgesics do nothing to encourage or support this process.

Back and neck pain is often caused by a fixated misaligned skeletal system that pinches nerves and focuses an inappropriate amount of movement on the regions of the body that remain flexible. This disproportionate sharing of movement often leads to acute pain due to muscle over-extension or nerve pinching. While the best long-term response to this problem is muscular-skeletal realignment, the residual tension often foils this restructuring by pulling the bones back out of position. The appropriate adjunctive therapy to the realignment is to relax the muscle tension and quell the excess nerve activity. None of these functions are accomplished by the standard treatment of menthol rubs or analgesics.

In fact, generally viewed, the present state of treating muscular-skeletal problems is to directly combat the symptoms. This is standard allopathic medical philosophy and works against the natural healing systems of the body. What is presented here is a set of therapeutic gels that are designed to support the healing activities of the body while producing sufficient relief to the user.

SUMMARY OF THE INVENTION

It is, therefore, an object of the present invention to provide water based synthetic gels for delivery of herbal extracts below the skin, to facilitate healing of muscular-skeletal problems through topical application.

Further, a method for treating musculoskeletal problems by applying a topical composition to a skin surface adjacent the musculoskeletal problem, the topical composition consisting essentially of herbal extracts in a water based synthetic gel and periodically repeating the step of applying as necessary for treatment of the musculoskeletal problem. The water based synthetic gel consists of water, Vitamin C, a carbomer, an antifungal, an anti-oxidant, a buffer and a chelate and zero alcohol. The herbal extracts are blends of the following herbs: St. John's Wort, White Willow, Yarrow, Poke, Lavender, Arnica, Comfrey, Devil's Claw, Witch Hazel, Celery Seed, Peppermint and Rosemary.

Other objects and advantages of the present invention will become apparent from the following detailed description, when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

The present invention provides a topical composition designed to facilitate healing of muscular-skeletal problems through topical application. In general, the topical composition includes a water-based gel having a mixture of complementary herbal extracts designed to encourage healing upon application to and absorption through the skin of an individual. In addition, an entire suite of topical compositions is provided. The variety of topical compositions is designed to implement a common approach to healing muscular-skeletal problems.

In accordance with a preferred embodiment of the present invention, the various topical compositions described below in greater detail all contain a number of common elements. The first function is to deliver the active herbal agents directly to the site of the injury. This is accomplished by making a water-based synthetic polymer gel of a full strength herbal decoction. The water-based gel is readily absorbed through the skin and acts as an effective transport mechanism for the critical herbal constituents to the site of the injury.

In contrast to the present invention, products that use salves with waxes and products that contain oils and petroleum based carriers are not readily bio-absorbable. Consequently, most of the active ingredients remain on the outside of the body where they cannot achieve their intended purpose. Using a water-based gel in accordance with the present invention allows for the manufacture of a topical composition that may be considered a full-strength herbal decoction carrier. This is due to the fact that most prior art topical herbal gels use organic based gelling agents and the herbal decoctions using natural or organic gelling agents are stabilized for bacterial and fungal growth by the use of 10% to 40% alcohol. This precludes the use of a water based gelling agent. The present topical composition uses a water-based preservative package consisting of a carbomer (called carbopol Ultrez 21 manufactured by Noveon), Vitamin C, Originox (manufactured by Rad Natural Technologies) and Germaben (manufactured by Sutton Laboratories). This package allows several years of shelf life without the use of alcohol.

As stated above, typical topical herbal gels use organic based gelling agents such as Guar Gum, Xanthan Gum, Methyl cellulose or Alginates. These gelling agents have several drawbacks. First, they tend to be mostly starch or fragile, short carbon chain molecules that are easily broken by heat, light and degrade over time. When they break, the gelling quality that they impart to the fluid in which they are used is lost and the gel turns "soupy". Second, since they are derived from plant material, there are many funguses that can digest them. Consequently when they are used in a topical product, a strong antifungal preservative needs to be added to prevent fungal growth. When large amounts of preservatives to inhibit the fungal growth are added to a topical herbal gel to keep the gel from being destroyed, the preservatives have been found to defeat the "natural healing" nature of a product. That is, the herbal extracts become less effective. Most purchasers of a natural product do not want to apply large concentrations of preservatives to their skin.

By using a fully synthetic polymer gelling agent, such as a carbomer alone or combined with UltraSil (a synthetic polymer manufactured by Noveon) instead of a plant derived agent, the present invention can use a much milder antifungal agent, such as Germaben alone or combined with Originox, an anti-oxidant, and small amounts of the antifungal and/or antifungal/anti-oxidant agent. While it seems ironic to use a fully synthetic polymer in a "natural" product, it actually allows the natural product to be more natural by not having as much preservative in it. The bacteria and fungus will not find the gelling agent supportive since it does not offer starches of simple carbon backbones to digest.

The natural gelling agents (simple starches and simple, small carbon based chains) require chemical stabilizers to keep them from degrading. They function by sticking to water in the host fluid. When they break due to heat or over time, they release their grip on the water and the gel gets soupy. The fully synthetic polymers are longer chains that bind to each other while physically containing the water. This interlocking of the polymer chains is a much more robust means of adding a stiff rheology to the host fluid. The benefit here is that one need not add chemical stabilizers to the product in order to protect the gelling agent and once again the product remains more natural because of the use of the synthetic gelling agent.

In an application where "all natural" seems the rule, a simple deviation to allow a fully synthetic ingredient actually allows the product as a whole to be more natural by enabling the use of fewer artificial stabilizers and preservatives.

The next critical function of the present topical composition is its ability to facilitate access for the body's repair agents to the regions needing repair. This is accomplished with herbal extracts that promote blood flow, lymphatic flow and waste product clearance in the area. For example, Arnica Montana or Arnica contains enzymes that digest and allow clearance of clots caused by impact or tissue damage. Clearing these injurious by-products from the region maintains access for the repairing macrophages and healing components to reach the region. Devil's Claw aids in the clearance of acids from the region of troubled joints so that they do not accumulate and cause pain and surface tissue degradation. In order for the body to repair the tissues, it must be able to move hystiocytes and lymphosites into the region. These then produce cytokines and bring in healing elements that morph into fibroblasts (the collagen factories) that lay down new ligament and tissue. Herbal ingredients that promote suppleness in muscles or relax the fibers, such as Rosemary, Valerian, Lavender and Cramp Bark, also aid in this regard by relaxing the muscle tissue and allow good cleansing flow of the interstitial fluids.

The next important task is to repair the damaged tissue. This is accomplished by encouraging the fibroblasts to produce large amounts of collagen. This collagen matrix acts as the latticework to support the new tissue cells. Herbal extracts such as Calendula and Comfrey are good "cell proliferators" which encourage new cell growth by stimulating their production. As animals age, the rate at which they create new cells diminishes in response to injury and the stimulation of new cell growth is a critical advantage to completing a sound healing result. For cases of torn or damaged ligaments, tendons or damaged sliding joint surfaces, the collagen matrix that is produced is paramount to the success of the healing process. In cases such as muscle fiber damage from exercise or heavy use, the new muscle fiber will contribute to the mass and increased strength that is desired from a workout.

The final area in which the present topical composition enhances the healing process is in relieving some of the pain of the region so that the user can tolerate the healing process. This can be accomplished with analgesic herbal extracts such as Meadow Sweet, Arnica or White Willow bark, to name a few. It is important to reduce some of the pain in the region so that the user is encouraged to apply the product for the requisite duration and with the requisite frequency to allow the medicinal herbal extracts the opportunity to perform their vital healing support activities.

In summary, topical composition composed of herbal, water-based gels provide water-based gels to facilitate penetration; with no alcohol, encouraging sound lymphatic and vascular flow to the region, activating and proliferating the generation of cells to repair the damage, and quelling the pain to encourage use.

Several exemplar embodiments of the present water-based gel composition are disclosed below.

EXAMPLE 1

Ingredients: Devil's Claw, White Willow, Poke, Arnica, Celery Seed, and Vitamin C in a natural, water-based gel.

This gel is intended to relieve the pain of arthritic joints. It contains herbs to facilitate the mending of these joints over time with continued use.

Devil's Claw: anti-inflammatory, anti-rheumatic
White Willow: analgesic
Comfrey: tissue repair
Arnica: healing facilitation
Celery Seed: toxin clearing from joints
Poke: anti-viral
Suggested Use: Apply liberally to affected region as needed
Ingredients: A proprietary blend of: Devil's Claw (anti-inflammatory), White Willow (pain relief), Comfrey (joint repair), Arnica (analgesic and tissue repair), Celery Seed (clears toxins from joints) and Poke (anti-viral) in a natural water-based gel.

This Joint Gel contains a specific set of herbs that are grouped to deal with all of the issues surrounding rheumatic joints. There are numerous causes for this condition, so in order to make one gel that works for as many people as possible, a multi-pronged approach is necessary. Some cases are caused by a viral attack of the joints while others are caused by a regenerative inflammation cycle. All cases require some pain relief and tissue repair. Often toxic metabolic by-products are insufficiently cleared from the joint area and cause irritation of the synovial surfaces. Devil's Claw is a good anti-inflammatory for joints helping to break the cycle of inflammation and stiffness. White Willow serves well as an analgesic relieving the pain. Celery seed clears toxins from joints and synovial surfaces. The Poke is effective as an anti-viral in the cases where the inflammation is actually instigated by a viral attack of the local tissues. In order to keep the area progressing in a direction of improvement, the Comfrey will incite the fibroblasts to repair the collagen surfaces at a higher rate.

By breaking the inflammation cycle while relieving pain, clearing the joints, facilitating repair and attenuating the viral attack, we treat the issue of joint pain in a holistic manner that is better in the long term than just taking pain-killers. Any of these herbs alone would provide some benefit, but the combination of these herbs treats the entire problem so that the condition can progress towards a higher state of comfort.

EXAMPLE 2

Ingredients: Arnica, Witch Hazel, White Willow, Comfrey, and Vitamin C in a natural, water-based gel.

Muscle Rescue is designed to relax muscles; releasing tension and blockage so that proper flow can clear the residuals from over-use. It also includes an analgesic for immediate relief of pain. Muscle fiber mending is supported to ensure sound repair.

Arnica: analgesic and facilitate healing
Witch Hazel: muscle limber and suppleness
White Willow: pain relief
Comfrey: muscle cell building
Suggested Use: Apply liberally to affected muscle groups as needed
Ingredients: A proprietary blend of: Arnica (pain relief and facilitates healing), Witch Hazel (promotes muscle limberness and suppleness), White Willow (analgesic) and Comfrey (muscle tissue repair) in a natural water-based gel.

This Muscle Gel contains a suite of herbs that are designed to provide pain relief while supporting the healing process. After periods of heavy use, muscle fiber is broken. This is the process that initiates muscle growth as the broken fibers re-build as multiple fibers. This process though requires special handling. Most products utilize menthols for pain relief While this relieves the symptoms, it does nothing to support the muscle's needs during the healing and rebuilding process. Arnica and White Willow provide analgesic (pain relief) while the enzymes of the Arnica break up the micro-clots from muscle fiber breakage to allow good blood flow to the region. This blood flow is important to allow essential constituents to reach the region for repair and building of new muscle cells. The Witch Hazel then plays upon this by promoting suppleness within the muscle so as to maintain the natural pumping action of movement to remove toxins via the lymphatic system. Comfrey is an essential part of the complete embodiment as it is a cell proliferator and encourages the formation of new muscle cells. The combination of these specific herbs not only relieves the pain of muscle over-use, it actually supports the body in rebuilding the tissues and maintains flexibility for proper toxin removal.

EXAMPLE 3

Ingredients: Comfrey, Arnica, Rosemary and Vitamin C in a natural, water-based gel.

This gel is intended to facilitate the repair of damaged tendons, ligaments and soft tissues. Also included are herbs to reduce inflammation and relieve pain associated with injured tendons and soft tissues.

Comfrey: heals torn and damaged tendons, ligaments and bones
Arnica: pain relief and tissue repairs
Rosemary: circulatory stimulant
Suggested Use: Apply liberally to affected region several times a day.
Ingredients: A proprietary blend of: Comfrey (restores torn and damaged tissue), Arnica (analgesic and healing) and Rosemary (increases circulation to the region) in a natural water-based gel.

This Tendon Gel is an herbal gel combination that is designed for the repair of tendons and ligaments. These tissues have a commonality in that they are poorly vascularized making it difficult for the body to get sufficient repair action to them and also in that they rely on fibroblasts to lay down collagen for repair. As our bodies age, the blood flow to these tissues becomes less and the quiescent level of fibroblast activity for maintenance of these tissues wanes. This combination makes the tendons and ligaments weaker and less able to fully repair in the limited inflammation time after an injury.

The group of herbs selected for Tendon Gel forms a synergistic triad by supporting the healing process and reducing pain. The Arnica offers analgesic (pain relieving) benefit while offering an enzyme which dissolves micro-clots that often block the flow of blood to the region of damage. The Rosemary increases circulation in the region by dilating the peripheral vasculature and the Comfrey incites the fibroblasts to utilize the constituents provided by the blood stream to produce reparative collagen to re-build the damaged tissue. While there are many ways to subdue the pain of an injury, in the case of tendon and ligament damage, one wants to accomplish this without reducing the inflammation. It is this inflammation that signals to the brain that reparative action is required. The Arnica relieves the pain without stopping this signal for repair and thus supports instead of thwarts the healing process. The Comfrey contains Allantoin, which increases the rate of cell formation so more fibroblasts are produced and more collagen is laid down. Of course, in order to build more collagen, one needs more of the constituents that are carried to the site by the blood stream. This is where the Rosemary with its blood flow enhancing action supports the Comfrey. While it may be known to use any of these herbs on a soft tissue injury individually, this particular combination of herbs is far more effective than any one alone.

EXAMPLE 4

Ingredients: St. John's Wort, Arnica, Lavender, White Willow, Yarrow, Comfrey and Vitamin C in a natural, water-based gel.

This gel is specifically designed to relax muscle spasm, increase cleansing flow in muscle tissue and reduce inflammation associated with common neck and back pain. It also contains analgesic herbs to reduce the pain during the period of recuperation.

St. John's Wort: quells nerve pain and inflammation
Arnica: pain relief and tissue repair
Lavender: antispasmodic
White Willow: analgesic
Yarrow: anti-inflammatory
Comfrey: to repair torn muscle tissue
Suggested Use: Apply liberally to affected region several times a day Ingredients: A proprietary blend of: St. John's Wort (quells nerve pain and inflammation), Arnica (pain relief and tisssue repair), Lavener (antispasmodic), White Willow (analgesic), Yarrow (anti-inflammatory) and Comfrey (tissue repair) in a natural water-based gel.

This Back & Neck Gel is formulated from a set of herbs that perform four functions: reduce the pain associated with back and neck pain, calm the nerves that are being irritated, facilitate the repair of any damaged tissues that could be exacerbating the cycle of pain and inflammation and relax spasming muscles. Other products may alleviate pain, some may even use muscle relaxing herbs, but this combination is more comprehensive in that it treats all of the aspects of the problem in a manner that is self-supporting to enhance the effect of each of the components. St. John's Wort allows the nerves to relax and stop sending "trauma" signals to the brain. It is important to stop these signals so that the muscle relaxing Lavender will be able to succeed in keeping the muscles from spasming. The Arnica, Yarrow and Willow ease the pain and reduce inflammation so that the user can be more comfortable and move more freely. The Comfrey will facilitate the healing of any damaged tissues that are contributing to the cycle of inflammation and pain. This allows the long-term benefit of the gel so that the condition will resolve and not require continued applications.

By having the correct combination of herbs to treat all of the aspects of the problem, we can bring it to a healing resolution instead of simply masking pain or constantly battling to keep muscles relaxed in an irritated-nerve condition.

EXAMPLE 5

Ingredients: St. John's Wort, White Willow, Yarrow, Poke, Lavender, Arnica and Vitamin C in a natural water-based gel.

In cases of acute nerve pain, this gel when applied to the primary site of irritation will reduce inflammation and calm the irritated nerves. It also contains analgesics to quell the pain and muscle relaxing herbs to mitigate the local trauma responsible for the irritation-causing fixation.

This gel can also be effectively used for Trigeminal Neuralgia when applied to the $5^{th}$ nerve as it exits the cranium above the ear along the inflamed length to the jaw.

St. John's Wort: quells nerve pain and inflammation
White Willow: analgesic
Yarrow: anti-inflammatory
Poke: anti-viral
Lavender: anti-spasmodic
Arnica: facilitate healing and pain relief
Suggested Use: Apply liberally to low-back and sacral region as needed Ingredients: A proprietary blend of: St. John's Wort (quells nerve pain and inflammation), White Willow (analgesic), Yarrow (anti-inflammatory), Lavender (anti-spasmodic), Arnica (pain relief and tissue repair) and Poke (anti-viral) in a natural water-based gel.

This Nerve Gel combination of herbs is intended primarily to quell nerve pain due to irritation of the nerve itself. The St. John's Wort offers this ability. Additionally, the White Willow offers prostaglandin blocking analgesic pain relief to stop signals of pain from reaching the brain. In keeping with the holistic treatment protocol, the source of the irritation must be dealt with. The Yarrow and Lavender act to reduce muscle spasm and tension that are often the cause of physical irritation of the nerve sheath. The Poke is a powerful antiviral. This is important as some conditions such as Trigeminal Neuralgia can be caused by virus attacking and damaging the schwann cells which comprise the protective sheath around nerves. Attenuating the inflammation due to this virus is critical in causing remission of the pain. The Arnica then aids in the repair of damaged tissue while the body returns to a healthier state.

EXAMPLE 6

Ingredients: Witch Hazel, Devils Claw, Arnica, Vitamin C and proprietary herbal extracts in a natural, water-based gel.

Designed to allow occasional heavy use of musculature by supporting good cleansing flow with muscle conditioning herbs. An analgesic component is added to quell pain during use. Tissue repair herbs are used to facilitate subsequent healing of the muscles required by peak use.

Witch Hazel: promotes muscle suppleness
Devil's Claw: proper muscle cleaness and joint support
Arnica: muscle pain relief and repair
White Willow: analgesic
Peppermint: Physical activity support
Suggested Use: Apply liberally to muscle before a strenuous workout or athletic competition.

Ingredients: A proprietary blend of: Witch Hazel (promotes muscle suppleness), Devil's Claw (muscle and joint cleansing), Arnica (muscle pain relief and repair), White Willow (analgesic) and Pepermint (physical activity support) in a natural water-based gel.

This Peak Performance Gel was designed to allow athletes to occasionally over-exert themselves without as severe a physiological penalty. Important races or even an occasional heavy training sessions require the ability to push ones body beyond the normal limits. Achieving this protection requires several key support features. Firstly, the suppleness of the muscles must be maintained to allow sound clearing of metabolic by-products from the region. This must be supported by micro-vascular dilation to enhance blood flow to the fibers. The Witch Hazel promotes muscle limberness while the Devil's Claw keeps joint inflammation low so that they can remain clear. These herbs act in concert to allow the athletes the most efficacious use of their musculature.

Of course, more endurance can be achieved by the temporary suppression of pain and so the White Willow acts in an analgesic manner to quell the pain of over-use. The Arnica assists in this pain mitigation while maintaining a free-flowing musculature by breaking up the micro-clots caused by muscle fiber breakage. These two herbs allow for over-exertion and also facilitate the healing necessary to deal with consequences. The peppermint provides physical activity support.

The resulting suites of topical compositions are water-based synthetic polymer gels designed to implement a holistic approach to the treatment of muscular-skeletal maladies. These topical compositions implement a much broader treatment than single herbal gels by treating the symptoms while supporting the healing process. Additionally, they are non-irritating to sensitive skin unlike menthol based salves. These gels are designed to rapidly penetrate the skin due to their water-based nature and thereby carry the vital compounds directly to the site of the damaged tissue.

A typical decoction will be made with from 1 to 10 grams of herbs per liter of water. The exact amount of each will depend on the particular herb, the function that it will be utilized for and the application area to which the final decoction will be applied. The gelling agent in this example may be a carbomer called carbopol that would be added in a concentration of 0.8% to 1%. To protect the carbomer from free ions, a chelate, such as EDTA (ethylenediaminetetraacetic acid) is used to scavange for free ions, could be added at a concentration of 0.05%. For shelf life enhancement by retarding bacterial and fungal growth, a preservative such as Germaben would be added at a concentration of 0.8%. From 1 to 2 grams of Ascorbic acid would be added to ensure a sufficiently low starting pH and as an anti-oxidant. Then a buffer such as NaOH (Sodium Hydroxide) would be introduced to facilitate the gelling process until the desired rheology has been attained.

Additional anti-oxidant protection could be secured by adding Origanox at a concentration of 0.05%. Further enhancement of the gel rheology can be achieved by the addition of UltraSil at a concentration of 0.9%.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for treating a musculoskeletal problem comprising applying an effective amount of a topical composition to a skin surface adjacent to the musculoskeletal problem of a subject in need thereof, the topical composition consisting essentially of a blend of herbal extracts in a water based synthetic gel containing zero alcohol; and periodically repeating the step of applying as necessary for treatment of the musculoskeletal problem, wherein the blend of herbal extracts is selected from the group consisting of A, B, C, D, E, and F, as follows;
    (A) Devil's Claw, White Willow, Comfrey, Arnica, Celery Seed and Poke (for treating trouble joints);
    (B) Arnica, Witch Hazel, White Willow and Comfrey (for treating muscle pain and repair);
    (C) Comfrey, Arnica and Rosemary (for treating damaged tendons, ligaments and soft tissues);
    (D) St. John's Wort, Arnica, Lavender, White Willow, Yarrow and Comfrey (for treating neck and back pain);
    (E) St. John's Wort, White Willow, Yarrow, Poke, Lavender, Arnica (for treating acute nerve pain); and
    (F) Witch Hazel, Devil's Claw and Peppermint (for muscle conditioning before peak use).

2. The method according to claim 1, wherein the water based gel consists of water, Vitamin C, a carbomer, an anti-fungal, an anti-oxidant, a buffer and a chelate.

\* \* \* \* \*